(12) United States Patent
Kornet et al.

(10) Patent No.: US 12,064,636 B2
(45) Date of Patent: Aug. 20, 2024

(54) PACING THERAPY SELECTION FOR HEART FAILURE TREATMENT

(71) Applicant: Medtronic, Inc., Minneapolis, MN (US)

(72) Inventors: Lilian Kornet, Berg en Terblijt (NL); Troy E. Jackson, Rogers, MN (US)

(73) Assignee: Medtronic, Inc., Minneapolis, MN (US)

( * ) Notice: Subject to any disclaimer, the term of this patent is extended or adjusted under 35 U.S.C. 154(b) by 523 days.

(21) Appl. No.: 17/361,500

(22) Filed: Jun. 29, 2021

(65) Prior Publication Data
US 2022/0032067 A1   Feb. 3, 2022

Related U.S. Application Data

(60) Provisional application No. 63/059,013, filed on Jul. 30, 2020.

(51) Int. Cl.
| | |
|---|---|
| A61N 1/365 | (2006.01) |
| A61N 1/02 | (2006.01) |
| A61N 1/362 | (2006.01) |
| A61N 1/368 | (2006.01) |
| A61N 1/37 | (2006.01) |

(52) U.S. Cl.
CPC ......... *A61N 1/36514* (2013.01); *A61N 1/025* (2013.01); *A61N 1/3624* (2013.01); *A61N 1/3688* (2013.01); *A61N 1/3702* (2013.01)

(58) Field of Classification Search
CPC .. A61N 1/025; A61N 1/3624; A61N 1/36514; A61N 1/3702
See application file for complete search history.

(56) References Cited

U.S. PATENT DOCUMENTS

| | | |
|---|---|---|
| 7,027,861 B2 | 4/2006 | Thompson |
| 8,233,980 B2 | 7/2012 | Pei |

(Continued)

OTHER PUBLICATIONS

Bianchi et al., "Increase of Ventricular Interval during Atrial Fibrillation by AV Node Vagal Stimulation: Chronic Clinical AVNS Download Study", http//circep.ahajournals.org, Jun. 4, 2015, 25 pages.

(Continued)

*Primary Examiner* — William J Levicky
(74) *Attorney, Agent, or Firm* — Mueting Raasch Group

(57) ABSTRACT

A method for heart failure management includes monitoring one or more sensor-based parameters for a patient to determine a pacing therapy. If the one or more parameters indicate atrial tachycardia or atrial fibrillation, a first pacing therapy is delivered. If the one or more parameters do not indicate atrial tachycardia or atrial fibrillation, it is determined whether the patient is asleep. If the patient is asleep, a second pacing therapy is delivered. If the one or more parameters do not indicate atrial tachycardia, atrial fibrillation, or that the patient is asleep, the patient's P-wave duration is evaluated with respect to a P-wave duration threshold value. When the patient's P-wave duration is determined to exceed the P-wave duration threshold value, a third pacing therapy is delivered, and when the patient's P-wave duration is determined to not exceed the P-wave duration threshold value, a fourth pacing therapy is delivered.

20 Claims, 6 Drawing Sheets

(56) References Cited

U.S. PATENT DOCUMENTS

| | | |
|---|---|---|
| 9,533,158 B2 * | 1/2017 | Min ................. A61N 1/368 |
| 9,737,720 B2 | 8/2017 | Meyer |
| 2003/0060850 A1 * | 3/2003 | Zhu .................. A61N 1/3627 |
| | | 607/9 |
| 2017/0050022 A1 | 2/2017 | Warman et al. |

OTHER PUBLICATIONS

International Search Report and Written Opinion from PCT Application No. PCT/US2021/041405 dated Oct. 26, 2021, 12 pages.

* cited by examiner

PACING THERAPY SELECTION FOR HEART FAILURE TREATMENT

RELATED PATENT APPLICATIONS

This application claims the benefit of U.S. Provisional Patent Application Ser. No. 63/059,013, filed on Jul. 30, 2020, which is incorporated by reference herein in its entirety.

BACKGROUND

The present technology is generally directed to pacing therapies for heart failure patients. In particular, the present technology is related to methods for selecting a pacing therapy based on monitored patient parameters.

Heart failure (HF) occurs when the heart muscle is unable to pump enough blood to meet the body's needs. The volume of blood pumped by the heart is determined by how well the heart squeezes (i.e., muscle contraction) and how well the heart relaxes and fills with blood. Ejection fraction is a measure of how much blood inside the left ventricle (LV) is pumped out with each contraction. When the left ventricle pumps, not all of the blood in the ventricle leaves. A normal ejection fraction is more than about 50%. Heart failure with preserved ejection fraction (HFpEF) occurs when the left ventricle does not fill with blood as well as normal, but the ventricle can pump well. For example, the ventricle is stiff, or has thick walls, such that the ventricle doesn't relax to fill with a normal volume of blood. Alternatively, when the muscle contraction is abnormal (e.g., the muscle is too weak to pump properly), the condition is referred to as heart failure with reduced ejection fraction (HFrEF).

Patients with HFpEF represent nearly half of the heart failure population and continue to increase in prevalence relative to patients with HFrEF. Although patients with HFpEF experience outcomes as poor as those for patients with HFrEF, no evidence-based therapy to improve mortality and morbidity exists. The present technology is directed to algorithms for selecting a pacing therapy for a heart failure patient, such as one with HFpEF, based on monitored patient parameters that also account for interactions among various pacing therapies. The algorithms and pacing therapies may be implemented by implantable medical devices (IMDs) such as implantable cardioverter defibrillators (ICDs), cardiovascular implantable electronic devices (CIEDs), pacemakers, and cardiac resynchronization therapy (CRT) devices that, in some cases, include defibrillation capability (CRT-D devices).

SUMMARY

Embodiments described herein are directed to a method for heart failure management. The method includes monitoring one or more sensor-based parameters for a patient. It is determined whether the one or more monitored sensor-based parameters indicate atrial tachycardia or atrial fibrillation, and when they do, a first pacing therapy is delivered. In response to the one or more sensor-based parameters not indicating atrial tachycardia or atrial fibrillation, it is determined whether the one or more monitored sensor-based parameters indicate the patient is asleep. In response to the one or more sensor-based parameters indicating the patient is asleep, a second therapy is delivered, and in response to the one or more sensor-based parameters not indicating atrial tachycardia, atrial fibrillation, or that the patient is asleep, it is determined whether the one or more monitored sensor-based parameters indicate the patient's P-wave duration exceeds a P-wave duration threshold value. In response to an indication that the patient's P-wave duration exceeds the P-wave duration threshold value, a third pacing therapy is delivered, and in response to an indication that the patient's P-wave duration does not exceed the P-wave duration threshold value, a fourth pacing therapy is delivered.

Other embodiments are directed to a method for heart failure management including monitoring one or more sensor-based parameters for a patient. It is determined whether the one or more monitored sensor-based parameters indicate atrial tachycardia or atrial fibrillation, and when they do, a first pacing therapy is delivered. In response to the one or more sensor-based parameters not indicating atrial tachycardia or atrial fibrillation, it is determined whether the one or more monitored sensor-based parameters indicate the patient is asleep. In response to the one or more sensor-based parameters indicating the patient is asleep, a second therapy is delivered.

Additional embodiments are directed to a method for heart failure management including monitoring one or more sensor-based parameters for a patient. It is determined whether the one or more monitored sensor-based parameters indicate atrial tachycardia or atrial fibrillation, and when they do, a first pacing therapy is delivered. In response to the one or more sensor-based parameters not indicating atrial tachycardia or atrial fibrillation, it is determined whether the one or more monitored sensor-based parameters indicate that the patient's P-wave duration exceeds a P-wave duration threshold value. If the one or more sensor-based parameters indicate that the patient's P-wave duration exceeds a P-wave duration threshold value, a second pacing therapy is delivered. If the one or more sensor-based parameters indicate that the patient's P-wave duration does not exceed a P-wave duration threshold value, a third pacing therapy is delivered.

Other embodiments are directed to a method for heart failure management including monitoring one or more sensor-based parameters for a patient. The method includes determining whether the one or more monitored sensor-based parameters indicate the patient's P-wave duration exceeds a P-wave duration threshold value. If the one or more sensor-based parameters indicate that the patient's P-wave duration exceeds a P-wave duration threshold value, a first atrioventricular node stimulation therapy is delivered. If the one or more sensor-based parameters indicate that the patient's P-wave duration does not exceed a P-wave duration threshold value, a second atrioventricular node stimulation therapy is delivered.

Further embodiments are directed to a heart failure management system. The system comprises one or more sensors to measure one or more sensor-based parameters, at least one storage component, and processing circuitry operably coupled to the one or more sensors and the at least one storage component. The processing circuitry is configured to determine whether the one or more monitored sensor-based parameters indicate atrial tachycardia or atrial fibrillation. When they do, the processing circuitry is configured to deliver a first pacing therapy. In response to the one or more sensor-based parameters not indicating atrial tachycardia or atrial fibrillation, the processing circuitry is configured to determine whether the one or more monitored sensor-based parameters indicate the patient is asleep. In response to the one or more sensor-based parameters indicating the patient is asleep, the processing circuitry is configured to deliver a second therapy, and in response to the one or more sensor-based parameters not indicating atrial tachycardia, atrial fibrillation, or that the patient is asleep, the processing circuitry is configured to determine whether the one or more monitored sensor-based parameters indicate the patient's P-wave duration exceeds a P-wave duration threshold value. In response to an indication that the patient's P-wave duration exceeds the P-wave duration threshold value, the processing circuitry is configured to deliver a third pacing therapy, and in response to an indication that the patient's P-wave duration does not exceed the P-wave duration threshold value, the processing circuitry is configured to deliver a fourth pacing therapy.

The above summary is not intended to describe each disclosed embodiment or every implementation of the present disclosure. The figures and the detailed description below more particularly exemplify illustrative embodiments.

BRIEF DESCRIPTION OF THE DRAWINGS

The discussion below refers to the following figures, wherein the same reference number may be used to identify the similar/same component in multiple figures. However, the use of a number to refer to a component in a given figure is not intended to limit the component in another figure labeled with the same number. The figures are not necessarily to scale.

DETAILED DESCRIPTION

The present disclosure is generally related to methods for selecting a pacing therapy for heart failure patients, e.g., patients with HFpEF, based on monitored patient parameters. A number of different pacing therapies have been proposed for treating HFpEF. These therapies include atrioventricular (AV) node stimulation to reduce ventricular rate during atrial fibrillation, nocturnal overdrive pacing, PR interval optimization by ventricular pacing, AV-node stimulation to decrease inflammation, and atrial pacing and rate response pacing. While each of these therapies provides individual benefits, they may be used in combination to harness positive interactions as well as mitigate or avoid negative interactions and improve outcomes for patients. Each of these therapies can be implemented with cardiac therapy systems and devices as described further below.

Figure 1:
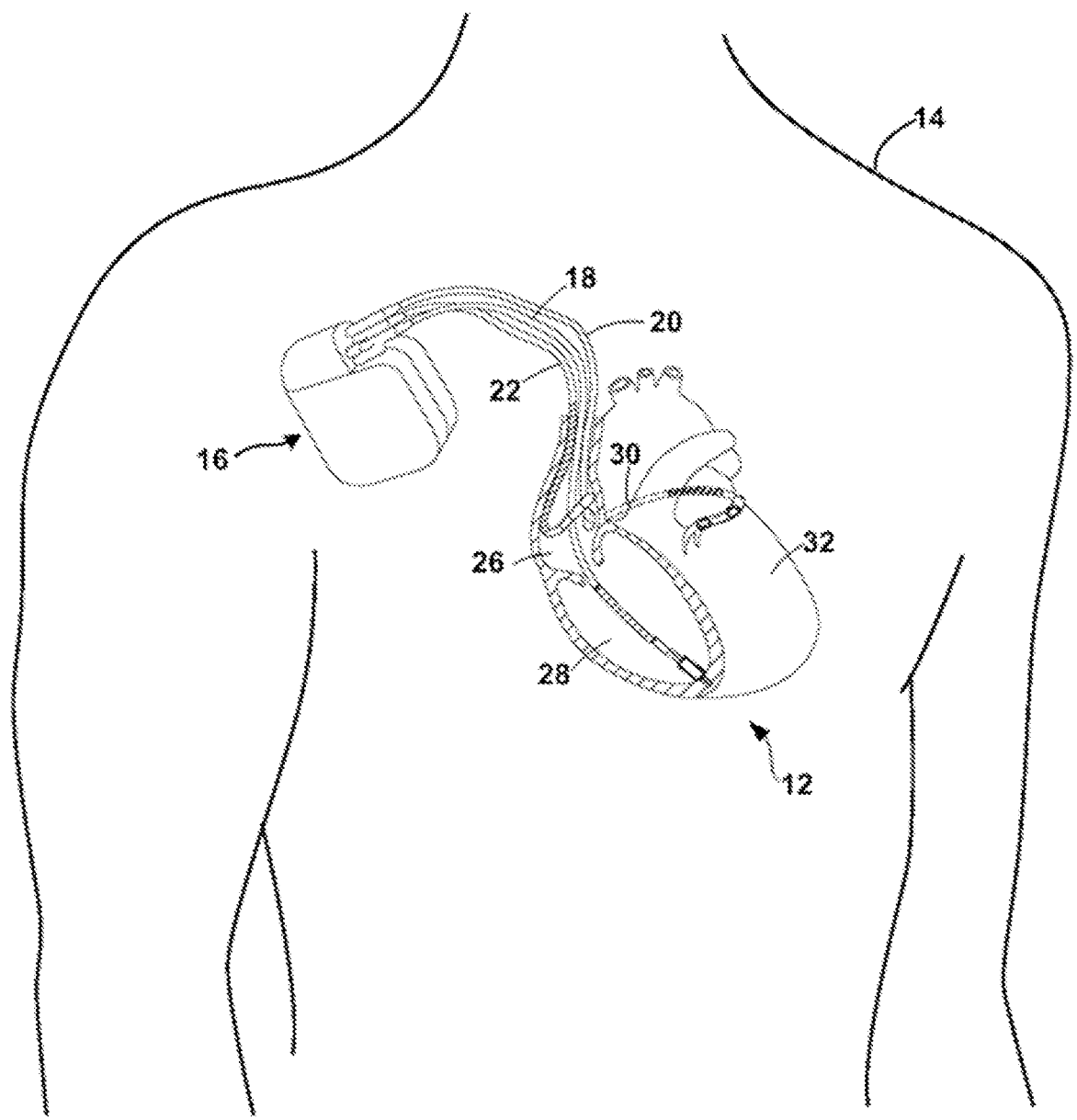
FIG. 1 is a diagram of a system including an IMD, in accordance with various embodiments described herein.

FIG. 1 is a conceptual diagram of an exemplary therapy system 10 that may be used to deliver pacing therapy, such as each of the above-mentioned therapies, to a patient 14. While patient 14 is shown as a human, patient 14 may also be a variety of other types of animal. The therapy system 10 may include an implantable medical device 16 (IMD), which may be coupled to leads 18, 20, 22. The IMD 16 may be, e.g., an implantable pacemaker, cardioverter, and/or defibrillator, that delivers, or provides, electrical signals (e.g., paces, etc.) to and/or senses electrical signals from the heart 12 of the patient 14 via electrodes coupled to one or more of the leads 18, 20, 22.

The leads 18, 20, 22 extend into the heart 12 of the patient 14 to sense electrical activity of the heart 12 and/or to deliver electrical stimulation to the heart 12. In the example shown in FIG. 1, the right ventricular (RV) lead 18 extends through one or more veins (not shown), the superior vena cava (not shown), and the right atrium 26, and into the right ventricle 28. The right atrial (RA) lead 22 extends through one or more veins and the vena cava, and into the right atrium 26 of the heart 12.

The IMD 16 may sense, among other things, electrical signals attendant to the depolarization and repolarization of the heart 12 via electrodes coupled to at least one of the leads 18, 20, 22. In some examples, the IMD 16 provides pacing therapy (e.g., pacing pulses) to the heart 12 based on the electrical signals sensed within the heart 12. The IMD 16 may be operable to adjust one or more parameters associated with the pacing therapy such as, e.g., pacing rate, R-R interval, A-V delay and other various timings, pulse width, amplitude, voltage, burst length, etc. Further, the IMD 16 may be operable to use various electrode configurations to deliver pacing therapy, which may be unipolar, bipolar, quadripolar, or further multipolar. Hence, a multipolar lead system may provide, or offer, multiple electrical vectors to pace from. A pacing vector may include at least one cathode, which may be at least one electrode located on at least one lead, and at least one anode, which may be at least one electrode located on at least one lead (e.g., the same lead, or a different lead) and/or on the casing, or can, of the IMD, or electrode apparatus. While improvement in cardiac function as a result of the pacing therapy may primarily depend on the cathode, the electrical parameters like impedance, pacing threshold voltage, current drain, longevity, etc. may be more dependent on the pacing vector, which includes both the cathode and the anode. The IMD 16 may also provide defibrillation therapy and/or cardioversion therapy via electrodes located on at least one of the leads 18, 20, 22. Further, the IMD 16 may detect arrhythmia of the heart 12, such as fibrillation of the ventricles 28, 32, and deliver defibrillation therapy to the heart 12 in the form of electrical pulses. In some examples, IMD 16 may be programmed to deliver a progression of therapies, e.g., pulses with increasing energy levels, until a fibrillation of the heart 12 is stopped.

Figure 2:
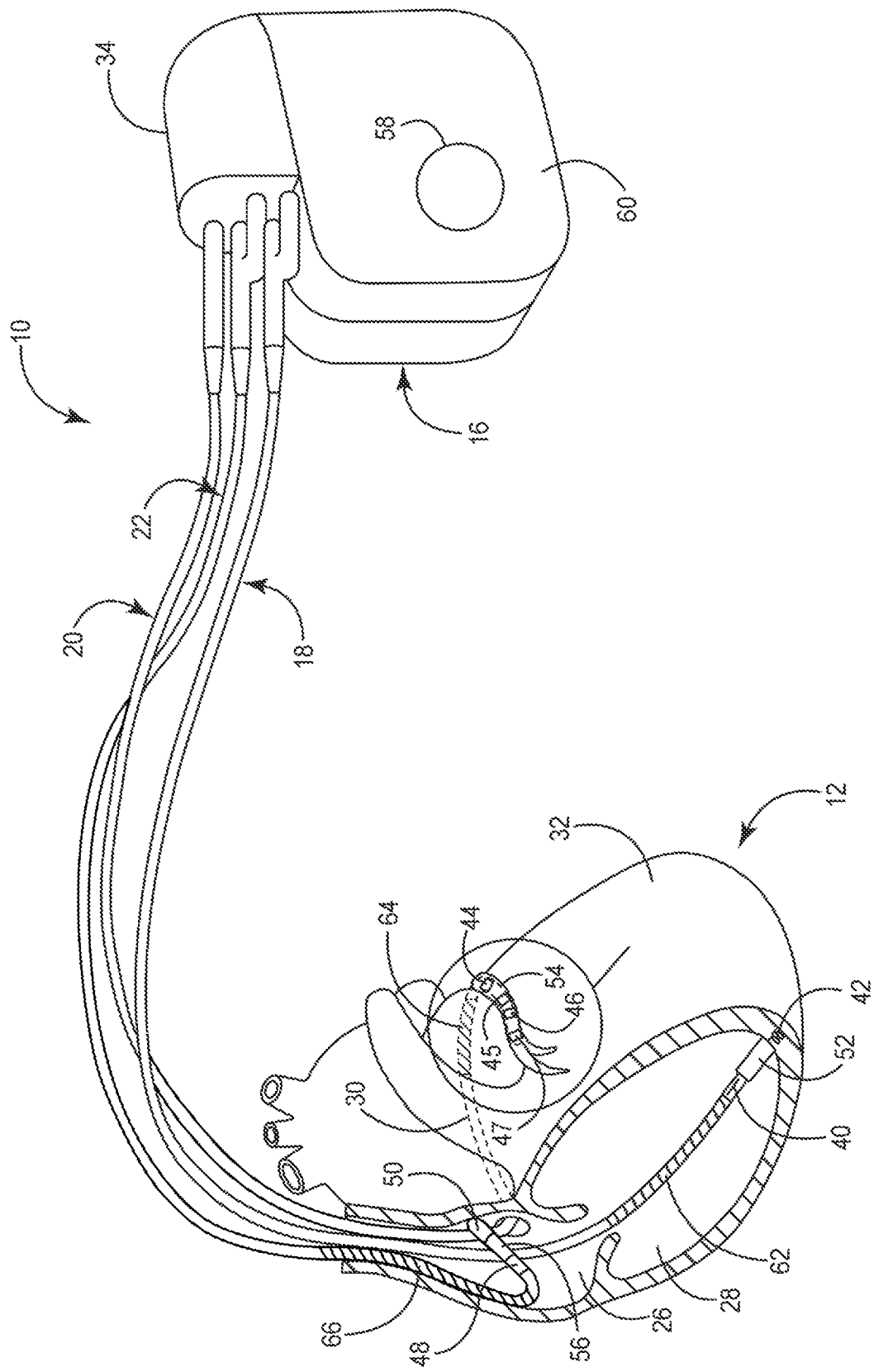
FIG. 2 is a diagram of the IMD of FIG. 1.

FIG. 2 is a conceptual diagram of the IMD 16 and the leads 18, 20, 22 of therapy system 10 of FIG. 1 in more detail. The leads 18, 20, 22 may be electrically coupled to a therapy delivery module (e.g., for delivery of pacing therapy), a sensing module (e.g., for sensing one or more signals from one or more electrodes), and/or any other modules of the IMD 16 via a connector block 34. In some examples, the proximal ends of the leads 18, 20, 22 may include electrical contacts that electrically couple to respective electrical contacts within the connector block 34 of the IMD 16. In addition, in some examples, the leads 18, 20, 22 may be mechanically coupled to the connector block 34 with the aid of set screws, connection pins, or another suitable mechanical coupling mechanism.

Each of the leads 18, 20, 22 includes an elongated insulative lead body, which may carry a number of conductors (e.g., concentric coiled conductors, straight conductors, etc.) separated from one another by insulation (e.g., tubular insulative sheaths). In the illustrated example, bipolar electrodes 40, 42 are located proximate to a distal end of the lead 18. In addition, bipolar electrodes 44, 45, 46, 47 are located proximate to a distal end of the lead 20 and bipolar electrodes 48, 50 are located proximate to a distal end of the lead 22.

The electrodes 40, 44, 45, 46, 47, 48 may take the form of ring electrodes, and the electrodes 42, 50 may take the form of extendable helix tip electrodes mounted retractably within the insulative electrode heads 52, 54, 56, respectively. Each of the electrodes 40, 42, 44, 45, 46, 47, 48, 50 may be electrically coupled to a respective one of the conductors (e.g., coiled and/or straight) within the lead body of its associated lead 18, 20, 22, and thereby coupled to a respective one of the electrical contacts on the proximal end of the leads 18, 20, 22.

The electrodes 40, 42, 44, 45, 46, 47, 48, 50 may further be used to sense electrical signals (e.g., morphological waveforms within electrograms (EGM)) attendant to the depolarization and repolarization of the heart 12. The electrical signals are conducted to the IMD 16 via the respective leads 18, 20, 22. In some examples, the IMD 16 may also deliver pacing pulses via the electrodes 40, 42, 44, 45, 46, 47, 48, 50 to cause depolarization of cardiac tissue within the patient's heart 12. In some examples, as illustrated in FIG. 2, the IMD 16 includes one or more housing electrodes, such as housing electrode 58, which may be formed integrally with an outer surface of a housing 60 (e.g., hermetically-sealed housing) of the IMD 16 or otherwise coupled to the housing 60. Any of the electrodes 40, 42, 44, 45, 46, 47, 48, 50 may be used for unipolar sensing or pacing in combination with the housing electrode 58. It is generally understood by those skilled in the art that other electrodes can also be selected to define, or be used for, pacing and sensing vectors. Further, any of electrodes 40, 42, 44, 45, 46, 47, 48, 50, 58, when not being used to deliver pacing therapy, may be used to sense electrical activity during pacing therapy.

As described in further detail with reference to FIG. 2, the housing 60 may enclose a therapy delivery module that may include a stimulation generator for generating cardiac pacing pulses and defibrillation or cardioversion shocks, as well as a sensing module for monitoring the electrical signals of the patient's heart (e.g., the patient's heart rhythm). The leads 18, 20, 22 may also include elongated electrodes 62, 64, 66, respectively, which may take the form of a coil. The IMD 16 may deliver defibrillation shocks to the heart 12 via any combination of the elongated electrodes 62, 64, 66 and the housing electrode 58. The electrodes 58, 62, 64, 66 may also be used to deliver cardioversion pulses to the heart 12. Further, the electrodes 62, 64, 66 may be fabricated from any suitable electrically conductive material, such as, but not limited to, platinum, platinum alloy, and/or other materials known to be usable in implantable defibrillation electrodes. Since electrodes 62, 64, 66 are not generally configured to deliver pacing therapy, any of electrodes 62, 64, 66 may be used to sense electrical activity and may be used in combination with any of electrodes 40, 42, 44, 45, 46, 47, 48, 50, 58. In at least one embodiment, the RV elongated electrode 62 may be used to sense electrical activity of a patient's heart during the delivery of pacing therapy (e.g., in combination with the housing electrode 58, or defibrillation electrode-to-housing electrode vector).

The above-described configuration of the therapy system 10 is merely one example. In other examples, the therapy system may include epicardial leads and/or patch electrodes instead of, or in addition to, the transvenous leads 18, 20, 22 illustrated in FIG. 1. In further embodiments, the therapy system 10 may be implanted in/around the cardiac space without transvenous leads (e.g., leadless/wireless pacing systems) or with leads implanted (e.g., implanted transvenously or using approaches) into the left chambers of the heart (in addition to or replacing the transvenous leads placed into the right chambers of the heart as illustrated in FIG. 1). In one example, the left ventricular (LV) coronary sinus lead 20 extends through one or more veins, the vena cava, the right atrium 26, and into the coronary sinus 30 to a region adjacent to the free wall of the left ventricle 32 of the heart 12. Further, in one or more embodiments, the IMD 16 need not be implanted within the patient 14. For example, the IMD 16 may deliver various cardiac therapies to the heart 12 via percutaneous leads that extend through the skin of the patient 14 to a variety of positions within or outside of the heart 12. In one or more embodiments, the system 10 may utilize wireless pacing (e.g., using energy transmission to the intracardiac pacing component(s) via ultrasound, inductive coupling, RF, etc.) and sensing cardiac activation using electrodes on the can/housing and/or on subcutaneous leads.

Other example therapy systems that provide electrical stimulation therapy to the heart 12 may include any suitable number of leads coupled to the IMD 16, and each of the leads may extend to any location within or proximate to the heart 12. Such other therapy systems may include three transvenous leads located as illustrated in FIGS. 1-2. Still further therapy systems may include a single lead that extends from the IMD 16 into the right atrium 26 or two leads that extend into a respective one of the right atrium 26 and the left atrium. In one example, the IMD 16, as a cardiac resynchronization therapy (CRT) device with a left ventricular (LV) lead may be useful for a HFpEF patient if there is a complete AV node block, as a LV lead can be more beneficial than a RV lead in such patients. In some examples, it can be desirable to deliver rate responsive pacing to the atrium for a HFpEF patient with chronotropic incompetence with an atrial lead (i.e. single chamber atrial system such as AAI) and atrial and ventricular lead system (i.e. dual chamber system such as DDD and VDD).

Figure 3A:
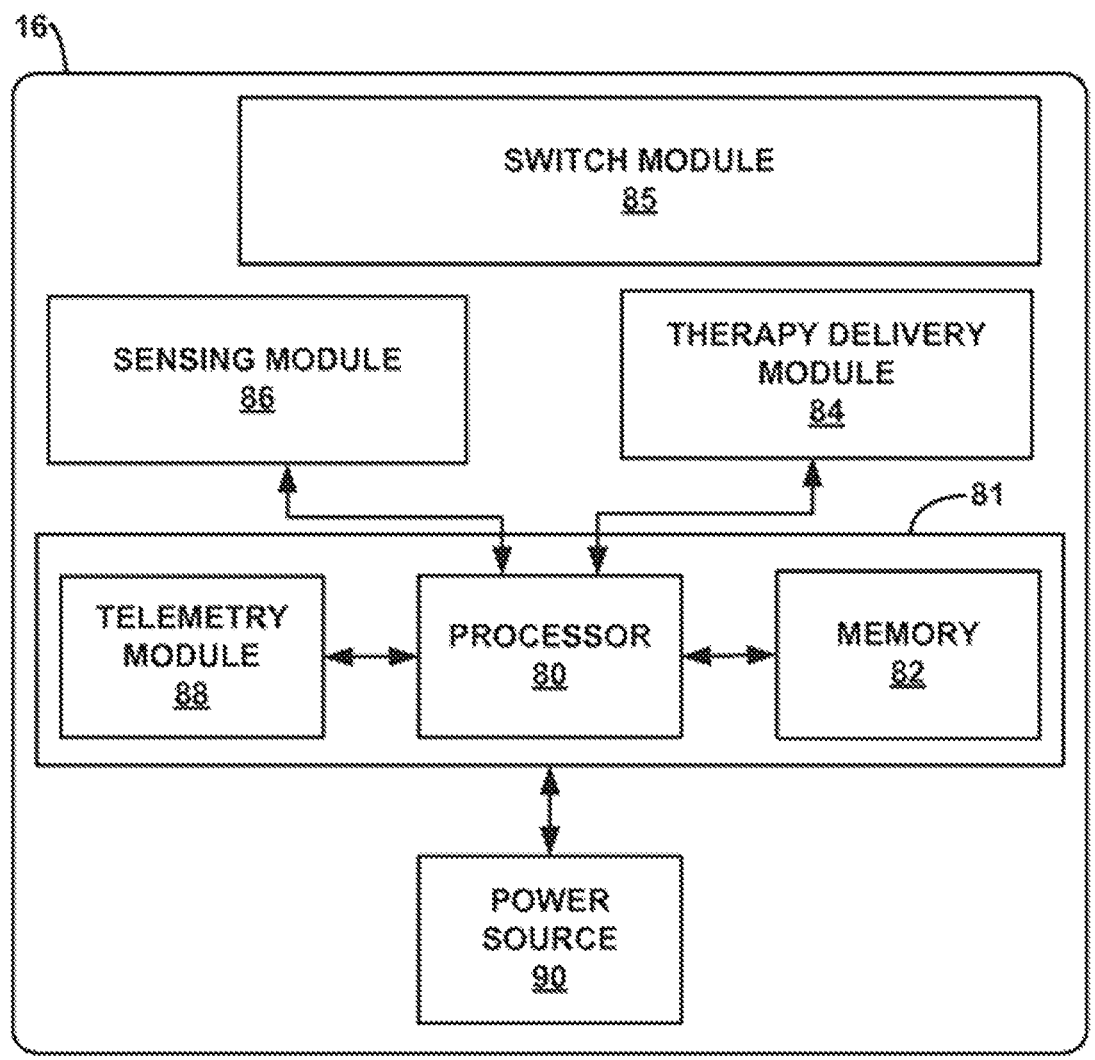
FIG. 3A is a block diagram of an IMD, e.g., of the systems of FIGS. 1-2, in accordance with embodiments described herein.

FIG. 3A is a functional block diagram of an example configuration of the IMD 16. As shown, the IMD 16 may include a control module 81, a therapy delivery module 84 (e.g., which may include a stimulation generator), a sensing module 86, and a power source 90. The control module, or apparatus, 81 may include a processor 80, memory 82, and a telemetry module, or apparatus, 88. The memory 82 may include computer-readable instructions that, when executed, e.g., by the processor 80, cause the IMD 16 and/or the control module 81 to perform various functions attributed to the IMD 16 and/or the control module 81 described herein. Further, the memory 82 may include any volatile, non-volatile, magnetic, optical, and/or electrical media, such as a random-access memory (RAM), read-only memory (ROM), non-volatile RAM (NVRAM), electrically-erasable programmable ROM (EEPROM), flash memory, and/or any other digital media.

The processor 80 of the control module 81 may include any one or more of a microprocessor, a controller, a digital signal processor (DSP), an application specific integrated circuit (ASIC), a field-programmable gate array (FPGA), and/or equivalent discrete or integrated logic circuitry. In some examples, the processor 80 may include multiple components, such as any combination of one or more microprocessors, one or more controllers, one or more DSPs, one or more ASICs, and/or one or more FPGAs, as well as other discrete or integrated logic circuitry. The functions attributed to the processor 80 herein may be embodied as software, firmware, hardware, or any combination thereof.

The control module 81 may control the therapy delivery module, or apparatus, 84 to deliver therapy (e.g., electrical stimulation therapy such as pacing) to the heart 12 according to a selected one or more therapy programs, which may be stored in the memory 82, and based on algorithms, or methods, described further below. More, specifically, the control module 81 (e.g., the processor 80) may control various parameters of the electrical stimulus delivered by the therapy delivery module 84 such as, e.g., A-V delays, pacing pulses with the amplitudes, pulse widths, frequency, or electrode polarities, etc., which may be specified by one or more selected therapy programs (e.g., A-V delay adjustment programs, pacing therapy programs, pacing recovery programs, capture management programs, etc.). As shown, the therapy delivery module 84 is electrically coupled to electrodes 40, 42, 44, 45, 46, 47, 48, 50, 58, 62, 64, 66, e.g., via conductors of the respective lead 18, 20, 22, or, in the case of housing electrode 58, via an electrical conductor disposed within housing 60 of IMD 16. Therapy delivery module 84 may be configured to generate and deliver electrical stimulation therapy such as pacing therapy to the heart 12 using one or more of the electrodes 40, 42, 44, 45, 46, 47, 48, 50, 58, 62, 64, 66.

For example, the therapy delivery module 84 may deliver pacing stimulus (e.g., pacing pulses) via ring electrodes 40, 44, 45, 46, 47, 48 coupled to leads 18, 20, 22 and/or helical tip electrodes 42, 50 of leads 18, 22. Further, for example, therapy delivery module 84 may deliver defibrillation shocks to the heart 12 via at least two of electrodes 58, 62, 64, 66. In some examples, therapy delivery module 84 may be configured to deliver pacing, cardioversion, or defibrillation stimulation in the form of electrical pulses. In other examples, therapy delivery module 84 may be configured to deliver one or more of these types of stimulation in the form of other signals, such as sine waves, square waves, and/or other substantially continuous time signals.

The IMD 16 may further include a switch module, or apparatus, 85 and the control module 81 (e.g., the processor 80) may use the switch module 85 to select, e.g., via a data/address bus, which of the available electrodes are used to deliver therapy such as pacing pulses for pacing therapy, or which of the available electrodes are used for sensing. The switch module 85 may include a switch array, switch matrix, multiplexer, or any other type of switching device suitable to selectively couple the sensing module, or apparatus, 86 and/or the therapy delivery module 84 to one or more selected electrodes. More specifically, the therapy delivery module 84 may include a plurality of pacing output circuits. Each pacing output circuit of the plurality of pacing output circuits may be selectively coupled, e.g., using the switch module 85, to one or more of the electrodes 40, 42, 44, 45, 46, 47, 48, 50, 58, 62, 64, 66 (e.g., a pair of electrodes for delivery of therapy to a bipolar or multipolar pacing vector). In other words, each electrode can be selectively coupled to one of the pacing output circuits of the therapy delivery module using the switching module 85.

The sensing module 86 is coupled (e.g., electrically coupled) to sensing apparatus, which may include, among additional sensing apparatus, the electrodes 40, 42, 44, 45, 46, 47, 48, 50, 58, 62, 64, 66 to monitor electrical activity of the heart 12, e.g., electrocardiogram (ECG)/electrogram (EGM) signals, etc. The ECG/EGM signals may be used to measure or monitor activation times (e.g., ventricular activations times, etc.), heart rate (HR), heart rate variability (HRV), heart rate turbulence (HRT), deceleration/acceleration capacity, deceleration sequence incidence, T-wave alternans (TWA), P-wave to P-wave intervals (also referred to as the P-P intervals or A-A intervals), R-wave to R-wave intervals (also referred to as the R-R intervals or V-V intervals), P-wave to QRS complex intervals (also referred to as the P-R intervals, A-V intervals, or P-Q intervals), QRS-complex morphology, ST segment (i.e., the segment that connects the QRS complex and the T-wave), T-wave changes, QT intervals, electrical vectors, etc.

The switch module 85 may also be used with the sensing module 86 to select which of the available electrodes are used, or enabled, to, e.g., sense electrical activity of the patient's heart (e.g., one or more electrical vectors of the patient's heart using any combination of the electrodes 40, 42, 44, 45, 46, 47, 48, 50, 58, 62, 64, 66). Likewise, the switch module 85 may also be used with the sensing module 86 to select which of the available electrodes are not to be used (e.g., disabled) to, e.g., sense electrical activity of the patient's heart (e.g., one or more electrical vectors of the patient's heart using any combination of the electrodes 40, 42, 44, 45, 46, 47, 48, 50, 58, 62, 64, 66), etc. In some examples, the control module 81 may select the electrodes that function as sensing electrodes via the switch module within the sensing module 86, e.g., by providing signals via a data/address bus.

In some examples, sensing module 86 includes a channel that includes an amplifier with a relatively wider pass band than the R-wave or P-wave amplifiers. Signals from the selected sensing electrodes may be provided to a multiplexer, and thereafter converted to multi-bit digital signals by an analog-to-digital converter for storage in memory 82, e.g., as an electrogram (EGM). In some examples, the storage of such EGMs in memory 82 may be under the control of a direct memory access circuit.

In some examples, the control module 81 may operate as an interrupt-driven device and may be responsive to interrupts from pacer timing and control module, where the interrupts may correspond to the occurrences of sensed P-waves and R-waves and the generation of cardiac pacing pulses. Any necessary mathematical calculations may be performed by the processor 80 and any updating of the values or intervals controlled by the pacer timing and control module may take place following such interrupts. A portion of memory 82 may be configured as a plurality of recirculating buffers, capable of holding one or more series of measured intervals, which may be analyzed by, e.g., the processor 80 in response to the occurrence of a pace or sense interrupt to determine whether the patient's heart 12 is presently exhibiting atrial or ventricular tachyarrhythmia.

The telemetry module 88 of the control module 81 may include any suitable hardware, firmware, software, or any combination thereof for communicating with another device, such as a programmer. For example, under the control of the processor 80, the telemetry module 88 may receive downlink telemetry from and send uplink telemetry to a programmer with the aid of an antenna, which may be internal and/or external. The processor 80 may provide the data to be uplinked to a programmer and the control signals for the telemetry circuit within the telemetry module 88, e.g., via an address/data bus. In some examples, the telemetry module 88 may provide received data to the processor 80 via a multiplexer.

The various components of the IMD 16 are further coupled to a power source 90, which may include a rechargeable or non-rechargeable battery. A non-rechargeable battery may be selected to last for several years, while a rechargeable battery may be inductively charged from an external device, e.g., on a daily or weekly basis.

Figure 3B:
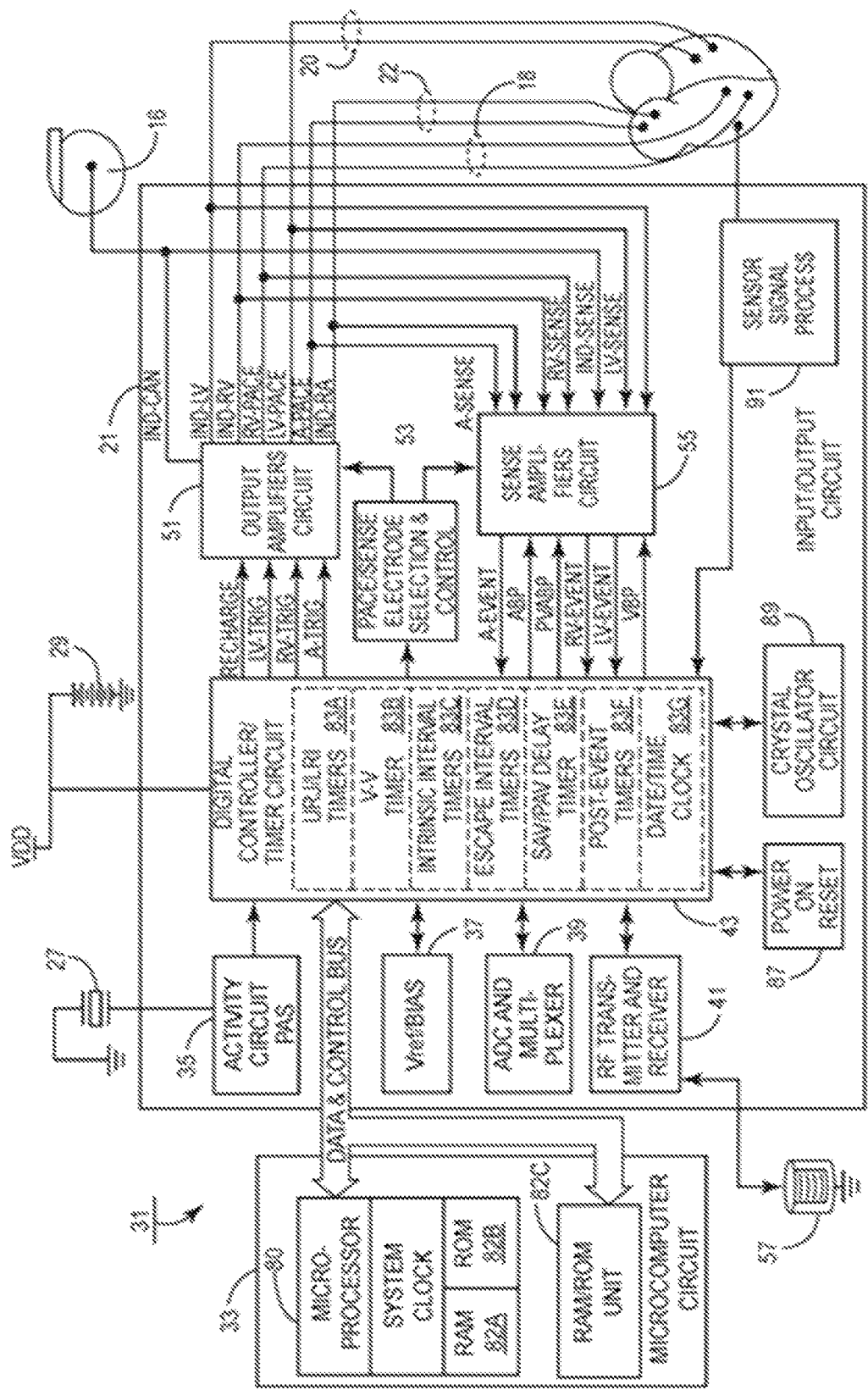
FIG. 3B is another block diagram of IMD (e.g., an implantable pulse generator) circuitry and associated leads employed in the systems of FIGS. 1-2.

FIG. 3B is a functional block diagram for an embodiment of IMD 16 that depicts bipolar RA lead 22, bipolar RV lead 18 without the LA CS pace/sense electrodes and coupled with an implantable pulse generator (IPG) circuit 31 having programmable modes and parameters of a bi-ventricular DDD/R type known in the pacing art. In turn, the sensor signal processing circuit 91 indirectly couples to the timing circuit 43 via data and control bus to microcomputer circuitry 33. The IPG circuit 31 is illustrated in a functional block diagram divided generally into a microcomputer circuit 33 and a pacing circuit 21. The pacing circuit 21 includes the digital controller/timer circuit 43, the output amplifiers circuit 51, the sense amplifiers circuit 55, the RF telemetry transceiver 41, the activity sensor circuit 35 as well as a number of other circuits and components described below.

Crystal oscillator circuit 89 provides the basic timing clock for the pacing circuit 21 while battery 29 provides power. Power-on-reset circuit 87 responds to initial connection of the circuit to the battery for defining an initial operating condition and similarly, resets the operative state of the device in response to detection of a low battery condition. Reference mode circuit 37 generates stable voltage reference and currents for the analog circuits within the pacing circuit 21. Analog-to-digital converter (ADC) and multiplexer circuit 39 digitize analog signals and voltage to provide, e.g., real time telemetry of cardiac signals from sense amplifiers 55 for uplink transmission via RF transmitter and receiver circuit 41. Voltage reference and bias circuit 37, ADC and multiplexer 39, power-on-reset circuit 87, and crystal oscillator circuit 89 may correspond to any of those used in illustrative implantable cardiac pacemakers.

If the IPG is programmed to a rate responsive mode, the signals output by one or more physiologic sensors are employed as a rate control parameter (RCP) to derive a physiologic escape interval. For example, the escape interval is adjusted proportionally to the patient's activity level developed in the patient activity sensor (PAS) circuit 35 in the example IPG circuit 31. The patient activity sensor 27 is coupled to the IPG housing and may take the form of a piezoelectric crystal transducer. The output signal of the patient activity sensor 27 may be processed and used as an RCP. Sensor 27 generates electrical signals in response to sensed physical activity that are processed by activity circuit 35 and provided to digital controller/timer circuit 43. Similarly, the illustrative systems, apparatus, and methods described herein may be practiced in conjunction with alternate types of sensors such as oxygenation sensors, pressure sensors, pH sensors, temperature sensors, respiration sensors, perfusion sensors, heart sound sensors, and heart rate sensors, for use in providing rate responsive pacing capabilities. For example, impedance can be measured using a ring electrode on the lead (e.g., RA or RV lead) and temperature can be measured by a sensor at the distal end of the lead. Alternately, QT time may be used as a rate indicating parameter, in which case no extra sensor is required. Similarly, the illustrative embodiments described herein may also be practiced in non-rate responsive pacemakers.

Data transmission to and from the external programmer is accomplished by way of the telemetry antenna 57 and an associated RF transceiver 41, which serves both to demodulate received downlink telemetry and to transmit uplink telemetry. Uplink telemetry capabilities may include the ability to transmit stored digital information, e.g., activity information, rate responsive pacing profiles, operating modes and parameters, EGM histograms, and other events, as well as real time EGMs of atrial and/or ventricular electrical activity and marker channel pulses indicating the occurrence of sensed and paced depolarizations in the atrium and ventricle.

Microcomputer 33 contains a microprocessor 80 and associated system clock and on-processor RAM and ROM chips 82A and 82B, respectively. In addition, microcomputer circuit 33 includes a separate RAM/ROM chip 82C to provide additional memory capacity. Microprocessor 80 normally operates in a reduced power consumption mode and is interrupt driven. Microprocessor 80 is awakened in response to defined interrupt events, which may include A-TRIG, RV-TRIG, LV-TRIG signals generated by timers in digital timer/controller circuit 43 and A-EVENT, RV-EVENT, and LV-EVENT signals generated by sense amplifiers circuit 55, among others. The specific values of the intervals and delays timed out by digital controller/timer circuit 43 are controlled by the microcomputer circuit 33 by way of data and control bus from programmed-in parameter values and operating modes. In addition, if programmed to operate as a rate responsive pacemaker, a timed interrupt, e.g., every cycle or every two seconds, may be provided in order to allow the microprocessor to analyze the activity sensor data and update the basic pacing rate as well as A-A, V-A, as applicable. In addition, the microprocessor 80 may also serve to define variable, operative A-V delay intervals, and the energy delivered to each ventricle and/or atrium.

In one embodiment, microprocessor 80 is a custom microprocessor adapted to fetch and execute instructions stored in RAM/ROM unit 82 in a conventional manner. It is contemplated, however, that other implementations may be suitable to practice the disclosed methods. For example, an off-the-shelf, commercially available microprocessor or microcontroller, or custom application-specific, hardwired logic, or state-machine type circuit may perform the functions of microprocessor 80.

Digital controller/timer circuit 43 operates under the general control of the microcomputer 33 to control timing and other functions within the pacing circuit 21 and includes a set of timing and associated logic circuits of which certain ones pertinent to the present disclosure are depicted. The depicted timing circuits include URI/LRI timers 83A, V-V delay timer 83B, intrinsic interval timers 83C for timing elapsed V-EVENT to V-EVENT intervals or V-EVENT to A-EVENT intervals, escape interval timers 83D for timing A-A, and/or V-A pacing escape intervals, an A-V delay interval timer 83E for timing the A-LVp delay (or A-RVp delay) from a preceding A-EVENT or A-TRIG, a post-ventricular timer 83F for timing post-ventricular time periods, and a date/time clock 83G.

The A-V delay interval timer 83E is loaded with an appropriate delay interval for one ventricular chamber (e.g., either an A-RVp delay or an A-LVp) to time-out starting from a preceding A-PACE or A-EVENT. The interval timer 83E triggers pacing stimulus delivery and can be based on one or more prior cardiac cycles (or from a data set empirically derived for a given patient).

The post-event timer 83F times out the post-ventricular time period following an RV-EVENT or LV-EVENT or a RV-TRIG or LV-TRIG and post-atrial time periods following an A-EVENT or A-TRIG. The durations of the post-event time periods may also be selected as programmable parameters stored in the microcomputer 33. The post-ventricular time periods include a post-ventricular atrial blanking period (PVARP), a post-atrial ventricular blanking period (PAVBP), a ventricular blanking period (VBP), and a ventricular refractory period (VRP) although other periods can be suitably defined depending, at least in part, on the operative circuitry employed in the pacing engine. The post-atrial time periods include an atrial refractory period (ARP) during which an A-EVENT is ignored for the purpose of resetting any A-V delay, and an atrial blanking period (ABP) during which atrial sensing is disabled. It should be noted that the starting of the post-atrial time periods and the A-V delays can be commenced substantially simultaneously with the start or end of each A-EVENT or A-TRIG or, in the latter case, upon the end of the A-PACE which may follow the A-TRIG. Similarly, the starting of the post-ventricular time periods and the V-A escape interval can be commenced substantially simultaneously with the start or end of the V-EVENT or V-TRIG or, in the latter case, upon the end of the V-PACE which may follow the V-TRIG. The microprocessor 80 also optionally calculates A-V delays, post-ventricular time periods, and post-atrial time periods that vary with the sensor-based escape interval established in response to the RCP(s) and/or with the intrinsic atrial and/or ventricular rate.

The output amplifiers circuit 51 contains a RA pace pulse generator (and a LA pace pulse generator if LA pacing is provided), a RV pace pulse generator, a LV pace pulse generator, and/or any other pulse generator configured to provide atrial and ventricular pacing. In order to trigger generation of an RV-PACE or LV-PACE pulse, digital controller/timer circuit 43 may utilize the algorithms described below.

The output amplifiers circuit 51 includes switching circuits for coupling selected pace electrode pairs from among the lead conductors and the IND-CAN electrode 20 to the RA pace pulse generator (and LA pace pulse generator if provided), RV pace pulse generator and LV pace pulse generator. Pace/sense electrode pair selection and control circuit 53 selects lead conductors and associated pace electrode pairs to be coupled with the atrial and ventricular output amplifiers within output amplifiers circuit 51 for accomplishing RA, LA, RV, and LV pacing.

The sense amplifiers circuit 55 contains sense amplifiers for atrial and ventricular pacing and sensing. High impedance P-wave and R-wave sense amplifiers may be used to amplify a voltage difference signal that is generated across the sense electrode pairs by the passage of cardiac depolarization wavefronts. The high impedance sense amplifiers use high gain to amplify the low amplitude signals and rely on pass band filters, time domain filtering and amplitude threshold comparison to discriminate a P-wave or R-wave from background electrical noise. Digital controller/timer circuit 43 controls sensitivity settings of the atrial and ventricular sense amplifiers 55.

The sense amplifiers may be uncoupled from the sense electrodes during the blanking periods before, during, and after delivery of a pace pulse to any of the pace electrodes of the pacing system to avoid saturation of the sense amplifiers. The sense amplifiers circuit 55 includes blanking circuits for uncoupling the selected pairs of the lead conductors and the IND-CAN electrode 20 from the inputs of the RA sense amplifier (and LA sense amplifier if provided), RV sense amplifier and LV sense amplifier during the ABP, PVABP and VBP. The sense amplifiers circuit 55 also includes switching circuits for coupling selected sense electrode lead conductors and the IND-CAN electrode 20 to the RA sense amplifier (and LA sense amplifier if provided), RV sense amplifier and LV sense amplifier. Again, sense electrode selection and control circuit 53 selects conductors and associated sense electrode pairs to be coupled with the atrial and ventricular sense amplifiers within the output amplifiers circuit 51 and sense amplifiers circuit 55 for accomplishing RA, LA, RV, and LV sensing along desired unipolar and bipolar sensing vectors.

Right atrial depolarizations or P-waves in the RA-SENSE signal that are sensed by the RA sense amplifier result in a RA-EVENT signal that is communicated to the digital controller/timer circuit 43. Similarly, left atrial depolarizations or P-waves in the LA-SENSE signal that are sensed by the LA sense amplifier, if provided, result in a LA-EVENT signal that is communicated to the digital controller/timer circuit 43. Ventricular depolarizations or R-waves in the RV-SENSE signal are sensed by a ventricular sense amplifier result in an RV-EVENT signal that is communicated to the digital controller/timer circuit 43. Similarly, ventricular depolarizations or R-waves in the LV-SENSE signal are sensed by a ventricular sense amplifier result in an LV-EVENT signal that is communicated to the digital controller/timer circuit 43. The RV-EVENT, LV-EVENT, and RA-EVENT, LA-SENSE signals may be refractory or non-refractory, and can inadvertently be triggered by electrical noise signals or aberrantly conducted depolarization waves rather than true R-waves or P-waves.

The techniques described in this disclosure, including those attributed to the IMD 16 and/or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices, or other devices. The term "module," "processor," or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure.

The systems, devices, and pacing therapy selection methods may be used to provide evaluation of a patient's cardiac health and/or evaluation and configuration of cardiac therapy being delivered to the patient. For example, the systems, devices, and pacing therapy selection methods may be used to determine and adjust a pacing therapy for HFpEF patients, as described further herein, based on patient parameters monitored over time.

As mentioned above, a number of different pacing therapies have been suggested for treating HFpEF. These include atrioventricular node stimulation (AVNS) to reduce ventricular rate during atrial fibrillation, atrial pacing and rate adaptive pacing, nocturnal overdrive pacing, PR interval optimization by ventricular pacing, and AVNS to decrease inflammation. These therapies are not administered discretely, or in a vacuum, as they interrelate and may be used in various combinations. As such, selecting one or more of these pacing therapies does not merely involve evaluating discrete patient parameters to select a single pacing therapy. Rather, methods discussed herein take into account each of the therapies and their potential interactions.

An increase in heart rate can lead to left ventricle wall thinning and dilatation. Myocyte cell loss and myocyte reactive hypertrophy are the major components of ventricular remodeling in pacing-induced dilated cardiomyopathy. Although this would exaggerate problems in heart failure patients with a decreased ejection fraction (e.g., HFrEF), this kind of remodeling is desirable for patients with HFpEF since they have a normal size ventricle with an increased wall thickness. Nocturnal overdrive pacing, e.g., increasing the heart rate (i.e., tachycardia pacing) to 100 beats/min for five hours at night via an implantable medical device, has been tested as a therapy to thin the left ventricle wall in a controlled fashion. Details regarding overdrive pacing are further provided in U.S. Pat. No. 9,737,720, which is herein incorporated by reference in its entirety.

Patients with a high ventricular rate during atrial fibrillation (AF) have an increased risk of receiving inappropriate implantable cardioverter defibrillator shocks. It has been shown that using AVNS during atrial fibrillation can reduce the ventricular rate to avoid such inappropriate and unnecessary shocks. Details regarding delivering AVNS during AF are further provided in U.S. Publication No. 2017/0050022, which is herein incorporated by reference in its entirety. However, if AVNS is delivered and delays the AV-node, the PR interval (interval from atrial activation (sense/pace) to ventricular activation) level should be improved, or optimized, by ventricular pacing since too much PR prolongation might be detrimental in heart failure patients.

With PR prolongation, atrial systole occurs too early in diastole, resulting in atrial contraction superimposed on the early left ventricular (LV) filling phase, and much earlier than the onset of LV systole. This leads to fusion of the E- and A-waves. A long PR interval is associated with electrophysiological abnormalities like atrial enlargement and myocardial fibrosis, atrioventricular nodal conduction delay and/or bundle branch/Purkinje fiber conduction delay, altered autonomic tone, and the effects of pharmacological interventions. PR interval prolongation is common in heart failure patients with reduced and normal ejection fraction and associated with worse survival, although it is not an independent predictor of outcome. In patients with solely atrial dyssynchrony and HFpEF, atrial pacing appears to provide a beneficial hemodynamic effect. While it is unknown if a long PR interval is a cause or an effect in heart failure, restoration of PR interval might increase LV filling. This may increase cardiac output and decrease mitral regurgitation.

AVNS can also be used to decrease inflammation. Proinflammatory cytokines are increased in HFpEF patients as compared with HFrEF patients and can predict future heart failure development. It has been shown that inflammation can be decreased via vagal stimulation. For example, the inflammatory reflex indicates that efferent vagal signaling could activate acetylcholine-dependent interaction with the alpha 7 nicotinic acetylcholine receptor subunit (a7nAChR) on monocytes and macrophages, resulting in reduced cytokine production. High-frequency inferior vena cava-inferior atrial ganglionated plexus stimulation for six hours has been shown to significantly decrease post-operative inflammation as shown by a decrease in IL-6, TNF-alfa, VEGF, and EGF serum levels. Intra-cardial stimulation of the nerves targeting the AV-node (vagal branch) (AVNS) could also affect inflammation within the heart and be effective in heart failure patients with a preserved ejection fraction.

To prevent the occurrence of arrhythmias, these AVNS therapies are given in bursts. As set forth above, AVNS has been proven to be effective to reduce the ventricular rate during AF and in this way has the potential to reduce inappropriate shocks in patients. The value to reduce inflammation in diastolic heart failure patients has already been shown for post-operative coronary artery bypass grafting patients.

Left atrial pacing can also be used to mitigate interatrial conduction block. Interatrial conduction block (IAB) is commonly defined as a P-wave duration≥120 ms on surface ECG. When fifty-five patients with HFpEF, were compared with thirty-three healthy individuals, it appeared that the inter- and intra-atrial dyssynchrony was strongly increased in patients with HFpEF compared to controls. Left atrial pacing therapy has also been used as a treatment to restore left ventricular active filling in HFpEF patients with no other known causes for heart failure than atrial dyssynchrony syndrome.

In addition, by making one or more of these pacing therapies pacing rate-adaptive, chronotropic incompetence can be limited. Chronotropic incompetence is common among HFpEF patients and is characterized by decreased heart rate response during activities of daily living or other activities requiring an increase in cardiac output (e.g., exercise). HFpEF patients with chronotropic incompetence often cannot elevate their sinus/atrial rate. Maximum exercise and peak heart rate achieved during exercise are both decreased for a patient with chronotropic incompetence.

Figure 4:
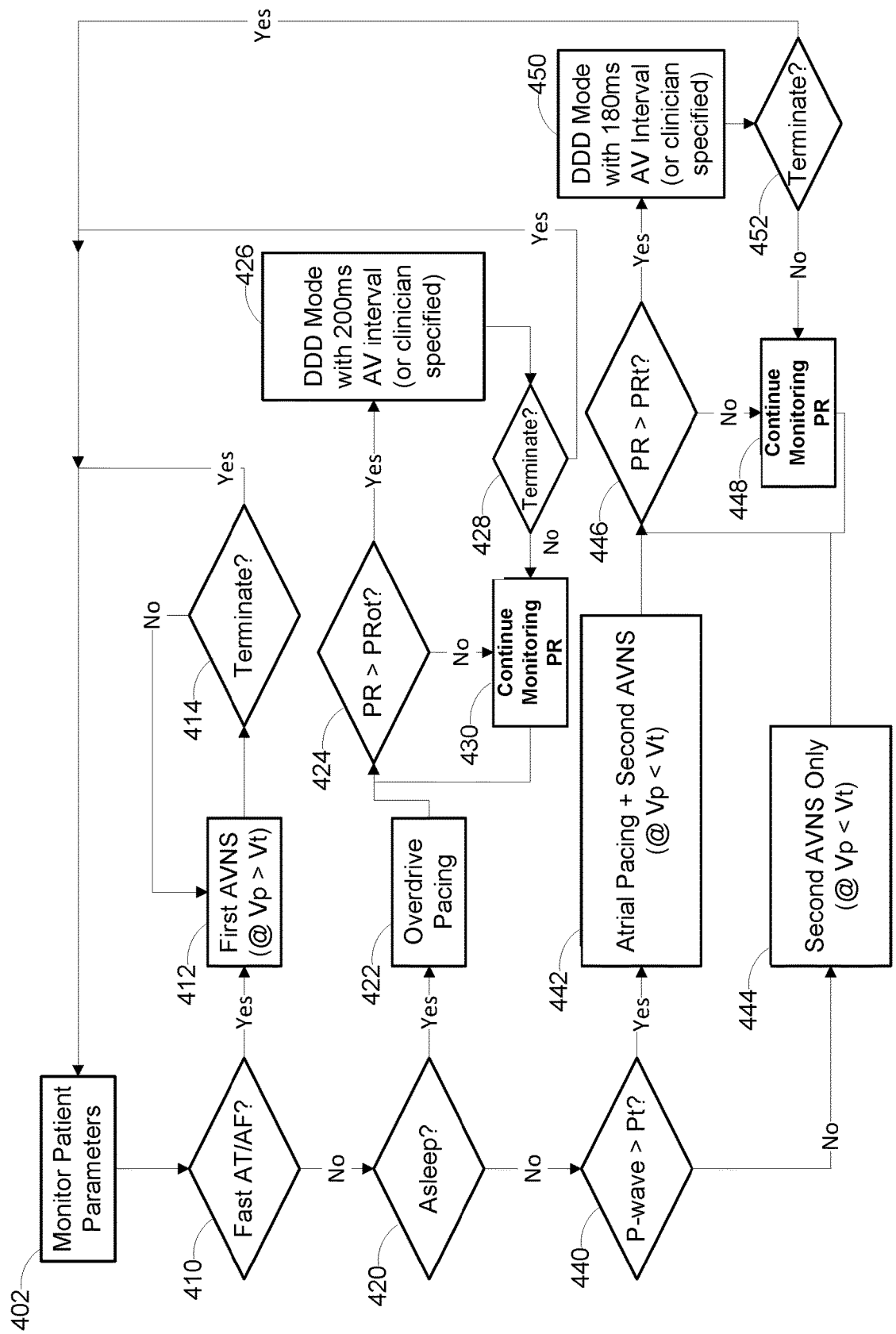
FIG. 4 is a flow diagram illustrating methods of selecting pacing therapies for a heart failure patient to be delivered by the IMD of FIG. 1, in accordance with various embodiments described herein.

FIG. 4 illustrates a flow diagram of a method for selecting one or more of the above-described pacing therapies while taking into account their potential interactions with each other for treating heart failure patients, particularly patients with HFpEF. The method begins by monitoring one or more patient parameters 402. The parameters may be any parameters that facilitate heart failure management such as one or more of thoracic impedance, heartrate (HR), atrial-to-atrial (AA) intervals to detect AF, ventricular rate during AF or rapid ventricular rate (RVR), daytime resting heartrate (which may be derived from a ventricular RR interval, wherein the R is the R of the QRS complex; may be measured supine), nighttime heartrate (NHR), heartrate variability (HRV), activity, cough, heart sounds (such as the S3 heart sound), patient weight, stroke volume (SV), cardiac output (CO), cardiac index (CI), filling pressure, systolic blood pressure (BP), and oxygen perfusion.

In general, one or more of the parameters may be device diagnostics captured by an IMD or patient wearable device. In some embodiments, one or more of the diagnostics may be captured by an external sensor or by user input.

Thoracic impedance may be measured using electrodes, for example, on an IMD and an intracardiac lead. For example, a housing-based electrode on the IMD housing (which may be described as a can) and an electrode on an RV coil lead may be used. A decreasing thoracic impedance may be used to indicate increasing cardiac preload and fluid accumulation.

HR or daytime resting heartrate may be measured using electrodes, for example, on an IMD (such as a housing-based electrode), an intracardiac lead, or an optical sensor on a patient wearable sensor. Elevated HR may be used as an indication of high heart failure risk. AA intervals may be measured using electrodes on, for example, an IMD (such as a housing-based electrode), an intracardiac lead, or an optical sensor on a patient wearable sensor. AA intervals may be used to distinguish between an atrial rhythm (such as AF) and a sinus rhythm. In some cases, AF may lead to worsening heart failure.

NHR may be measured using electrodes, for example, on an IMD (such as a housing-based electrode), an intracardiac lead, or an optical sensor on a patient wearable sensor. Elevated NHR may indicate elevated autonomic tone, and NHR may also be used to determine whether a patient is asleep.

HRV may be measured using electrodes, for example, on an IMD (such as a housing-based electrode), an intracardiac lead, or an optical sensor on a patient wearable sensor. Decreased HRV may be used to indicate elevated sympathetic tone and autonomic imbalance. Decreased HRV may be associated with elevated HR.

Activity may be measured using a motion sensor, such as an inertial measurement unit (IMU), in the IMD or patient wearable sensor. Activity may be used to indicate overall functional status of the patient including whether a patient is asleep. For example, decrease in activity may occur as a patient's risk of worsening heart failure increases.

Heart sounds, such as the S3 heart sound, may be measured using, for example, an accelerometer, a piezoelectric sensor, or microphone on an IMD. The presence of the S3 heart sound may be used to indicate elevated pulmonary atria pressure and may also be used to indicate increased risk of worsening heart failure.

Patient weight may be measured, for example, using a weight scale. Increased weight may be used to indicate fluid accumulation.

SV may be measured, for example, indirectly using an optical sensor and tissue oxygen sensor on an IMD or patient wearable sensor. Decreased SV may be used to indicate worsening heart failure.

Oxygen perfusion may be measured, for example, using an optical sensor on an IMD or patient wearable sensor. Decreased oxygen perfusion may be used to indicate worsening heart failure. Oxygen perfusion may be associated with, or correlated with, CO.

CO may be determined, for example, based on SV and HR. CO may be calculated by multiplying SV and HR. CO may be used to indicate worsening heart failure.

CI may be determined, for example, based on CO normalized to a patient's body surface area. CI may be used to indicate worsening heart failure. In some embodiments, CI may be used instead of CO, for example, when the patient's body surface area is known.

Filling pressure may be measured using a pressure sensor located, for example, in the left atrium or in the pulmonary artery. Elevated filling pressure may be used to indicate worsening heart failure.

Systolic BP may be measured, for example, using a wearable cuff. In general, BP may be used to guide intervention. Elevated BP may be used to indicate that certain interventions for worsening heart failure may be used. BP lower than a threshold may be used to indicate that certain interventions for worsening heart failure may be excluded.

Ventricular rate during AF or RVR may be measured using electrodes, for example, on an IMD (such as a housing-based electrode), an intracardiac lead, or an optical sensor on a patient wearable sensor. RVR may be used to indicate worsening heart failure.

An accelerometer and/or piezo electric sensor can be used to measure heart sounds, such as the S3 and S4 heart sounds. Heart sounds may emerge as the patient gains fluid and heart failure begins to worsen.

In general, heart sounds are associated with mechanical vibrations of a patient's heart and the flow of blood through the heart valves and, thus, may be highly correlated with pressure gradients across heart valves and blood pressure. Heart sounds may be not only due to vibrations of and pressure within the heart, but may also be due to the entire cardiohemic system, e.g., blood, heart, great arteries, etc. Heart sounds may recur with each cardiac cycle and are separated and classified according to the activity associated with the vibration.

The first heart sound is referred to as "S1," and can be thought of as the vibration sound made by the heart during closure of the atrioventricular, or AV, valves, i.e., the mitral valve and tricuspid valve. The S1 sound can sometimes be broken down into the M1 sound component, from the closing of the mitral valve, and the T1 sound component, from the closing of the tricuspid valve. The second heart sound is referred to as "S2," and results from the closure of the semilunar valves, i.e., the pulmonary and aortic valves. The S2 heart sound can be thought of as marking the beginning of diastole. The S2 sound can also be broken down into component parts. The P2 sound component is from the closing of the pulmonary valve, and the A2 sound component is from the closing of the aortic valve. The third and fourth heart sounds are referred to as "S3" and "S4," respectively, and can be conceptualized as related to filling of the ventricles during diastole. S3 is due to rapid filling of the ventricles and can occur when the ventricular wall is not relaxed when a large volume of blood flows into the ventricles from the atria. S4 is caused by blood rapidly filling into the ventricles from the atria due to atrial contraction.

These parameters may be monitoring constantly or on varying schedules and at any suitable rate depending on the parameter and/or patient's condition.

The parameters are monitored to detect atrial tachycardia (AT) and/or atrial fibrillation (AF), such as fastly conducted AT or AF 410. If it is determined that the one or more parameters indicate that the patient is experiencing AT or AF, a first pacing therapy is delivered 412. The first pacing therapy may be a first AVNS where the stimulation is delivered at a pacing voltage ($V_p$) greater than a threshold voltage ($V_t$). The threshold voltage is based on the amplitude necessary to produce prolongation of the atrioventricular conduction time by at least 25%, and examples of the threshold voltage are about 4V or in a range of 3V to 10V. As discussed above, the first AVNS pacing therapy is delivered to reduce ventricular rate during atrial fibrillation or tachycardia to reduce the administration of inappropriate shocks.

The first AVNS is delivered in bursts with a predetermined pulse train. The AVNS pulse trains are illustrated in connection with FIG. 5 and discussed further below. An example first AVNS pulse train may be described as VsApppp+As, which represents a ventricle sense followed 30 ms later by multiple atrial stimulations (e.g., 4). More specifically, the Apppp is a pulse train in atrium synchronized on QRS=Vsense or Vpace with voltage between four and eight volts, 20 ms apart, and a pulse width between 0.5 and 1.5 ms. The "+As" indicates that an atrial sense (or multiple atrial senses) are not triggered by the atrial pulse train but is separate. The pulses are delivered in the refractory period of the ventricle so as not to induce ventricular tachycardia or ventricular fibrillation. The first AVNS pacing therapy may also be used in combination with rate adaptive pacing techniques. An example later pulse train may involve the Vsense becoming a Vpace if a slower obtained rate requires pacing. Such a pulse train may be described as Vs/pAppppppp-As-As-Vp which represents a ventricular sensor or pace followed by six atrial pacing bursts, an atrial sense, an atrial sense, and a ventricular pace if the ventricular rate will reach a lower rate. In a case of atrial arrhythmia, there could be multiple pulse trains implemented in a cardiac cycle.

After delivering one atrioventricular node stimulation pulse train, parameters are evaluated to determine whether termination criteria have been met 414. Example termination criteria may include whether the first AVNS pacing therapy is effective in reducing the mean ventricular rate (e.g., response time is a programmable setting, nominal value, five beats). Further termination criteria may include whether during the AVNS (e.g., after the response time), a short RR interval occurs in the detection zone to ensure safety for the patient; a predetermined programmable interval time (e.g., maximum thirty seconds); or whether the detection of a real ventricular fibrillation occurs during the AVNS pacing therapy. Any one or more of these termination criteria may be used alone or in combination to determine whether to halt the first AVNS pacing therapy. If the programmed terminal criteria are met, the method returns to monitoring patient parameters 402. If the termination criteria is not met, the method returns to delivering another sequence of the first AVNS pacing therapy. For additional safety, the first AVNS pacing therapy may not be delivered in episodes with a mean ventricular interval below a threshold such as 260 ms, since short V-V intervals are common in oversensing scenarios and uncommon in inappropriate shocks by rapidly conducted AF.

If the one or more monitored patient parameters do not indicate a patient is experiencing fastly conducted atrial tachycardia or atrial fibrillation, it is determined whether one or more patient parameters indicate that the patient is asleep 420. If the parameters indicate that the patient is asleep, a second pacing therapy is delivered 422. In certain embodiments, the second pacing therapy is nocturnal overdrive pacing therapy. While the therapy is referred to as "nocturnal" it does not need to be administered during nighttime hours. Rather, the overdrive pacing is delivered when the patient is inactive for an extended period of time, which is typically when the patient is asleep to avoid the body self-regulating. This may, or may not be, during the night. The overdrive pacing therapy is delivered at a predetermined beats per minute (e.g., 100 bpm) for a predetermined amount of time (e.g., five hours).

During the overdrive pacing therapy, the patient's atrioventricular interval (PR) is evaluated with respect to an overdrive PR threshold interval (PRot) 424 to automatically modulate the type of therapy (e.g., atrial based or DDD pacing) within the overdrive pacing treatment. The overdrive PR threshold interval may be in a range of about 240-300 ms, with an example threshold of 240 ms. The overdrive PR threshold is selected to limit the PR so that the resulting RP interval is 300 ms or greater. If the patient's PR does not exceed the PR threshold interval, the PR is continued to be monitored while the overdrive pacing therapy is delivered 430. If the patient's PR equals or exceeds the PR threshold interval, a further pacing therapy is delivered simultaneously with the overdrive pacing in order to adjust, or optimize, the patient's PR 426. For example, the further pacing therapy may be DDD mode pacing with a preset AV interval (e.g., 200 ms). Alternatively, a clinician may program a preset AV interval specific to the patient's condition or computed by the implantable device to ensure the resulting RP interval is at least 300 ms. After delivering the further pacing therapy, it is determined whether termination criteria are met 428. For example, if the patient's AV interval shortens to an acceptable and predetermined rate (e.g., below 240 ms), the further pacing therapy is terminated and the method returns to overdrive atrial pacing without ventricular pacing 422. Alternatively, if the predetermined time for the overdrive pacing has been achieved, the overdrive pacing therapy will terminate and the method returns to monitoring patient parameters 402. However, if termination criteria are not met, the patient's PR will continue to be monitored while the overdrive pacing therapy is delivered 430.

If the one or more monitored patient parameters do not indicate that the patient is experiencing atrial tachycardia or atrial fibrillation and that the patient is not asleep, one or more pacing therapies may be delivered to reduce inflammation. Since anti-inflammatory pacing can result in nervous system remodeling, it is implemented less frequently and off-cycle (e.g., at night). To select a therapy, the patient's P-wave duration (i.e., time it takes to get right and left atria from start to finish) is evaluated with respect to a P-wave duration threshold 440. Interatrial conduction block (IAB) is commonly defined as a P-wave duration of equal to or greater than 120 ms on a surface ECG; therefore, 120 ms may be an example P-wave duration threshold.

If the one or more patient parameters indicate that the patient has IAB (e.g., a P-wave duration greater than or equal to 120 ms), a third pacing therapy is delivered 442. The third pacing therapy may be anti-inflammatory pacing (e.g., a second, different type of AVNS) coupled with atrial pacing. However, the stimulation for the second AVNS is delivered at a pacing voltage ($V_p$) less than a threshold voltage ($V_t$), e.g., the same threshold voltage discussed above with respect to the first AVNS sequence. The same threshold voltage may be used for both analyses in the therapy selection method. Alternatively, a separate buffer between the two may be used. For example, the voltage thresholds may be programmed such that 6V are needed to get extension of PR interval for the first AVNS discussed above, but stimulation at 2V may be used for anti-inflammatory (second) AVNS in order to preserve battery life and lower the risk of symptoms for the patient.

Also, as discussed above, the second AVNS is delivered in bursts with a predetermined pulse train. An example second AVNS pulse train may be described as Vs+Appppppp, which represents a ventricle sense with multiple atrial pacing bursts (e.g., 6). However, the Vs could also be Vp (ventricle pace stimulation). As above, the "+" indicates that the atrial pacing is not triggered on the Vs but is separate (e.g., there may be a time delay between Vs and the pulse train in the atrium). In other embodiments, the atrial pulse train could be triggered on atrial pace. In further embodiments an example pulse train of VsAppppppp+As, would refer to triggering the pulse in ventricular refractory period synchronized on QRS, i.e., triggered on ventricular sense. As set forth above, the pulse train has a lower voltage (e.g., 1-4V), but the same frequency as the first AVNS therapy (50

Hz, i.e., pulses 20 ms apart). The pulses in the refract period atrium are delivered so as not to induce atrial tachycardia or atrial fibrillation. The second AVNS pacing therapy may also be used in combination with rate adaptive pacing techniques. An example pulse train may be described as Apppppp-Vs (Vrate is not delayed)-Apppppp which represents six atrial paces followed by a ventricular sense and another sequence of five atrial pacing bursts.

Alternatively, if the one or more patient parameters indicate that the patient does not have IAB (e.g., a P-wave duration less than 120 ms), a fourth pacing therapy is delivered 442. The fourth pacing therapy may be anti-inflammatory pacing (e.g., a second, different type of AVNS) alone. Again, the stimulation for the second AVNS is delivered at a pacing voltage ($V_p$) less than a threshold voltage ($V_t$), e.g., the same threshold voltage discussed above with respect to the first AVNS sequence or another voltage value. Also, as discussed above, the second AVNS is delivered in bursts with a predetermined pulse train. However, the pulse train for AVNS here differs from that for a patient with IAB. An example second AVNS pulse train for the fourth pacing therapy may be described as Vs+Asppppp, which represents a ventricle sense with the pulse train triggered by an atrial sense followed by multiple atrial pacing bursts (e.g., 5). The pulses in the refract period atrium are delivered so as not to induce atrial tachycardia or atrial fibrillation. The second AVNS pacing therapy may again also be used in combination with rate adaptive pacing techniques. An example pulse train for the fourth pacing therapy may be described as Asppppp-Vs (Vrate is not delayed)-Apppppp which represents an atrial sense and five atrial paces followed by a ventricular sense and another sequence of five atrial pacing bursts.

During the third and/or fourth pacing therapy, the patient's atrioventricular interval (PR) is evaluated with respect to a PR threshold interval ($PR_t$) 446 to automatically modulate the type of therapy (e.g., atrial based or DDD pacing) within the anti-inflammatory pacing treatment. The PR threshold interval may be in a range of about 180-350 ms, with an example threshold of 200 ms, which is a common point among patients where negative effects of extended PR interval begin to manifest as less efficient pump function. If the patient's PR does not exceed the PR threshold interval, the PR is continued to be monitored while the third/fourth anti-inflammatory pacing therapy is delivered 448. If the patient's PR equals or exceeds the PR threshold interval, a further pacing therapy is delivered in order to adjust, or optimize, the patient's PR 450. For example, the further pacing therapy may be DDD mode pacing with a preset AV interval (e.g., 180 ms). The further pacing involves a ventricular pace after 180 ms with either an atrial sense or an atrial pace. Alternatively, a clinician may program a preset AV interval specific to the patient's condition.

After delivering the further pacing therapy, the anti-inflammatory pacing is continued or the pacing therapy is terminated to return to monitoring patient parameters 402. The determination is effectively a response to side effects of the stimulation or changing patient conditions. For example, if the desired stimulation is reached or the patient's intrinsic AV conduction becomes shorter than the DDD AV interval, the third/fourth pacing therapy may be terminated. In further embodiments, the anti-inflammatory pacing may be continued for a predetermined time or until a predetermined AV interval is obtained during either the anti-inflammatory pacing or the further pacing therapy. When returning to anti-inflammatory pacing, the patient's PR will continue to be monitored while the third/fourth anti-inflammatory pacing therapy is delivered 448.

Figure 5:
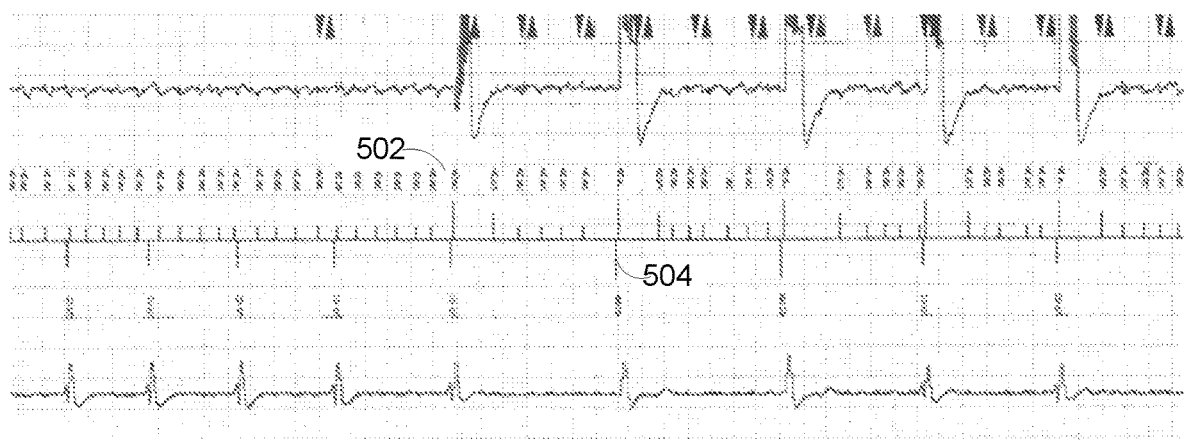
FIG. 5 is an atrial electrogram showing an example pulse train for atrioventricular node stimulation and the effects on ventricular rate during atrial fibrillation.

The AVNS pacing therapies are further illustrated by the atrial electrogram of FIG. 5. FIG. 5 displays an episode of AF and shows a typical example of the effect of AVNS during a test on ventricular rate during AF (e.g., 412 of the method of FIG. 4). There is rapid and irregular ventricular rate at the left part of the tracing, but at the black triangles 502, AVNS is activated. In FIG. 5, the pulse train is indicated with only "Ap" which above is referred to as Apppp to better indicate multiple stimulations. Immediately after the QRS complex, AVNS (8V, 1.5 ms, synchronized on QRS) is applied and ventricular rate instantly becomes slower. Here it even necessitates ventricular pacing 504, demonstrating strong modulation of the vagus nerve.

While multiple pacing therapies have been proposed and tested for patients with HFpEF, there is no coordinated pacing strategy in place for these patients. The methods described herein provide guidance for selecting one or more pacing therapies alone, or in combination, that account for the interoperability (or lack thereof) among the various pacing therapies. These methods may be provided as programmable instructions to a heart failure patient's implantable medical device to select an appropriate pacing therapy protocol.

Illustrative Embodiments

The technology described herein is defined in the claims. However, below is provided a non-exhaustive listing of non-limiting embodiments. Any one or more of the features of these embodiments may be combined with any one or more features of another example, embodiment, or aspect described herein.

In illustrative Embodiment 1, a method for heart failure management comprises monitoring one or more sensor-based parameters for a patient. If the one or more parameters indicate atrial tachycardia or atrial fibrillation, a first pacing therapy is delivered. If the one or more parameters do not indicate atrial tachycardia or atrial fibrillation, it is determined whether the patient is asleep. If the patient is asleep, a second pacing therapy is delivered. If the one or more parameters do not indicate atrial tachycardia, atrial fibrillation, or that the patient is asleep, the patient's P-wave duration is evaluated with respect to a P-wave duration threshold value. When the patient's P-wave duration is determined to exceed the P-wave duration threshold value, a third pacing therapy is delivered, and when the patient's P-wave duration is determined to not exceed the P-wave duration threshold value, a fourth pacing therapy is delivered.

In illustrative Embodiment 2, a method comprises the method of Embodiment 1 wherein the first pacing therapy is a first atrioventricular node stimulation sequence at a voltage greater than a threshold value. In illustrative Embodiment 3, a method comprises the method of any one of the preceding Embodiments wherein the second pacing therapy is overdrive pacing delivered at a predetermined frequency for a predetermined amount of time. In illustrative Embodiment 4, a method comprises the method of any one of the preceding Embodiments wherein the third pacing therapy comprises atrial pacing and a second atrioventricular node stimulation sequence at a voltage less than the threshold value. In illustrative Embodiment 5, a method comprises the method of any one of the preceding Embodiments wherein the fourth pacing therapy comprises the second atrioventricular node stimulation sequence at a voltage less than the threshold value.

In illustrative Embodiment 6, a method comprises the method of any one of the preceding Embodiments wherein the P-wave duration threshold value is 120 ms. In illustrative Embodiment 7, a method comprises the method of any one of the preceding Embodiments wherein the patient has heart failure with preserved ejection fraction.

In illustrative Embodiment 8, a method for heart failure management comprises monitoring one or more sensor-based parameters for a patient. It is determined whether the one or more monitored sensor-based parameters indicate atrial tachycardia or atrial fibrillation, and when they do, a first pacing therapy is delivered. In response to the one or more sensor-based parameters not indicating atrial tachycardia or atrial fibrillation, it is determined whether the one or more monitored sensor-based parameters indicate the patient is asleep. In response to the one or more sensor-based parameters indicating the patient is asleep, a second therapy is delivered.

In illustrative Embodiment 9, a method comprises the method of any one of the preceding Embodiments wherein the first pacing therapy is an atrioventricular node stimulation sequence at a voltage greater than a threshold value. In illustrative Embodiment 10, a method comprises the method of any one of the preceding Embodiments wherein the second pacing therapy is overdrive pacing delivered at a predetermined frequency for a predetermined amount of time.

In illustrative Embodiment 11, a method comprises the method of any one of the preceding Embodiments further comprising determining whether the patient's atrioventricular interval exceeds a threshold interval in response to delivering the overdrive pacing. If the patient's atrioventricular interval exceeds the threshold interval, DDD mode pacing is delivered with a predetermined atrioventricular interval, and if the patient's atrioventricular interval does not exceed the threshold interval, the patient's atrioventricular interval is monitored.

In illustrative Embodiment 12, a method for heart failure management comprises monitoring one or more sensor-based parameters for a patient. It is determined whether the one or more monitored sensor-based parameters indicate atrial tachycardia or atrial fibrillation, and when they do, a first pacing therapy is delivered. In response to the one or more sensor-based parameters not indicating atrial tachycardia or atrial fibrillation, it is determined whether the one or more monitored sensor-based parameters indicate that the patient's P-wave duration exceeds a P-wave duration threshold value. If the one or more sensor-based parameters indicate that the patient's P-wave duration exceeds a P-wave duration threshold value, a second pacing therapy is delivered. If the one or more sensor-based parameters indicate that the patient's P-wave duration does not exceed a P-wave duration threshold value, a third pacing therapy is delivered.

In illustrative Embodiment 13, a method comprises the method of Embodiment 12 wherein the first pacing therapy comprises a first atrioventricular node stimulation sequence at a first voltage greater than a threshold value. In illustrative Embodiment 14, a method comprises any one of Embodiments 12 and 13 wherein the second pacing therapy comprises atrial pacing and a second atrioventricular node stimulation sequence at a second voltage less than the threshold value. In illustrative Embodiment 15, a method comprises any one of Embodiments 12 through 14 wherein the third pacing therapy comprises the second atrioventricular node stimulation sequence at a third voltage less than the threshold value.

In illustrative Embodiment 16, a method for heart failure management comprises monitoring one or more sensor-based parameters for a patient. The method includes determining whether the one or more monitored sensor-based parameters indicate the patient's P-wave duration exceeds a P-wave duration threshold value. If the one or more sensor-based parameters indicate that the patient's P-wave duration exceeds a P-wave duration threshold value, a first atrioventricular node stimulation therapy is delivered. If the one or more sensor-based parameters indicate that the patient's P-wave duration does not exceed a P-wave duration threshold value, a second atrioventricular node stimulation therapy is delivered.

In illustrative Embodiment 17, a method comprises the method of Embodiment 16 wherein the first atrioventricular node stimulation therapy comprises atrial pacing and an atrioventricular node stimulation sequence at a voltage less than a threshold. In illustrative Embodiments 18, a method comprises the method of one of Embodiments 16 and 17 wherein the second atrioventricular node stimulation therapy is the atrioventricular node stimulation sequence at a voltage less than the threshold.

In illustrative Embodiment 19, a method comprises the method of any one of Embodiments 16 through 18 further comprising determining whether the patient's atrioventricular interval exceeds a threshold interval in response to delivering the first or second atrioventricular node stimulation therapy. In response to the patient's atrioventricular interval exceeding the threshold interval, DDD mode pacing is delivered with a predetermined atrioventricular interval, and in response to the patient's atrioventricular interval not exceeding the threshold interval, the patient's atrioventricular interval is monitored.

In illustrative Embodiment 20, a system for heart failure management comprises one or more sensors to measure one or more sensor-based parameters, at least one storage component, and processing circuitry operably coupled to the one or more sensors and the at least one storage component. The processing circuitry is configured to determine whether the one or more monitored sensor-based parameters indicate atrial tachycardia or atrial fibrillation. When they do, the processing circuitry is configured to deliver a first pacing therapy. In response to the one or more sensor-based parameters not indicating atrial tachycardia or atrial fibrillation, the processing circuitry is configured to determine whether the one or more monitored sensor-based parameters indicate the patient is asleep. In response to the one or more sensor-based parameters indicating the patient is asleep, the processing circuitry is configured to deliver a second therapy, and in response to the one or more sensor-based parameters not indicating atrial tachycardia, atrial fibrillation, or that the patient is asleep, the processing circuitry is configured to determine whether the one or more monitored sensor-based parameters indicate the patient's P-wave duration exceeds a P-wave duration threshold value. In response to an indication that the patient's P-wave duration exceeds the P-wave duration threshold value, the processing circuitry is configured to deliver a third pacing therapy, and in response to an indication that the patient's P-wave duration does not exceed the P-wave duration threshold value, the processing circuitry is configured to deliver a fourth pacing therapy.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

All references and publications cited herein are expressly incorporated herein by reference in their entireties for all purposes, except to the extent any aspect directly contradicts this disclosure.

All scientific and technical terms used herein have meanings commonly used in the art unless otherwise specified. The definitions provided herein are to facilitate understanding of certain terms used frequently herein and are not meant to limit the scope of the present disclosure.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein. The use of numerical ranges by endpoints includes all numbers within that range (e.g. 1 to 5 includes 1, 1.5, 2, 2.75, 3, 3.80, 4, and 5) and any range within that range.

The foregoing description has been presented for the purposes of illustration and description. It is not intended to be exhaustive or to limit the embodiments to the precise form disclosed. Many modifications and variations are possible in light of the above teachings. Any or all features of the disclosed embodiments can be applied individually or in any combination and are not meant to be limiting, but purely illustrative. It is intended that the scope of the invention be limited not with this detailed description, but rather, determined by the claims appended hereto.

What is claimed is:

1. A heart failure management system comprising:
one or more sensors to measure one or more sensor-based parameters;
at least one storage component; and
processing circuitry operably coupled to the one or more sensors and the at least one storage component, the processing circuitry configured to:
determine whether the one or more monitored sensor-based parameters indicate atrial tachycardia or atrial fibrillation;
deliver a first pacing therapy in response to the one or more sensor-based parameters indicating atrial tachycardia or atrial fibrillation;
determine whether the one or more monitored sensor-based parameters indicate the patient is asleep in response to the one or more sensor-based parameters not indicating atrial tachycardia or atrial fibrillation;
deliver a second pacing therapy in response to the one or more sensor-based parameters indicating the patient is asleep;
determine whether the one or more monitored sensor-based parameters indicate the patient's P-wave duration exceeds a P-wave duration threshold value in response to the one or more sensor-based parameters not indicating the patient is asleep, atrial tachycardia, or atrial fibrillation;
deliver a third pacing therapy in response to the one or more sensor-based parameters indicating the patient's P-wave duration exceeds a P-wave duration threshold value; and
deliver a fourth pacing therapy in response to the one or more sensor-based parameters not indicating the patient's P-wave duration exceeds a P-wave duration threshold value.

2. A method for heart failure management comprising:
monitoring one or more sensor-based parameters for a patient;
determining whether the one or more monitored sensor-based parameters indicate atrial tachycardia or atrial fibrillation;
delivering a first pacing therapy in response to the one or more sensor-based parameters indicating atrial tachycardia or atrial fibrillation;
determining whether the one or more monitored sensor-based parameters indicate the patient is asleep in response to the one or more sensor-based parameters not indicating atrial tachycardia or atrial fibrillation;
delivering a second pacing therapy in response to the one or more sensor-based parameters indicating the patient is asleep;
determining whether the one or more monitored sensor-based parameters indicate the patient's P-wave duration exceeds a P-wave duration threshold value in response to the one or more sensor-based parameters not indicating the patient is asleep, atrial tachycardia, or atrial fibrillation;
delivering a third pacing therapy in response to the one or more sensor-based parameters indicating the patient's P-wave duration exceeds the P-wave duration threshold value; and
delivering a fourth pacing therapy in response to the one or more sensor-based parameters not indicating the patient's P-wave duration exceeds the P-wave duration threshold value.

3. The method of claim 2, wherein the first pacing therapy is a first atrioventricular node stimulation sequence at a voltage greater than a threshold value.

4. The method of claim 3, wherein the third pacing therapy comprises atrial pacing and a second atrioventricular node stimulation sequence at a voltage less than the threshold value.

5. The method of claim 4, wherein the fourth pacing therapy comprises the second atrioventricular node stimulation sequence at a voltage less than the threshold value.

6. The method of claim 2, wherein the second pacing therapy is overdrive pacing delivered at a predetermined frequency for a predetermined amount of time.

7. The method of claim 2, wherein the P-wave duration threshold value is 120 ms.

8. The method of claim 2, wherein the patient has heart failure with preserved ejection fraction.

9. A method for heart failure management comprising:
monitoring one or more sensor-based parameters for a patient;
determining whether the one or more monitored sensor-based parameters indicate atrial tachycardia or atrial fibrillation;
delivering a first pacing therapy in response to the one or more sensor-based parameters indicating atrial tachycardia or atrial fibrillation;

determining whether the one or more monitored sensor-based parameters indicate the patient is asleep in response to the one or more sensor-based parameters not indicating atrial tachycardia or atrial fibrillation; and delivering a second pacing therapy in response to the one or more sensor-based parameters indicating the patient is asleep.

10. The method of claim 9, wherein the first pacing therapy is an atrioventricular node stimulation sequence at a voltage greater than a threshold value.

11. The method of claim 9, wherein the second pacing therapy is overdrive pacing delivered at a predetermined frequency for a predetermined amount of time.

12. The method of claim 11, further comprising:
determining whether the patient's atrioventricular interval exceeds a threshold interval in response to delivering the overdrive pacing;
delivering DDD mode pacing with a predetermined atrioventricular interval in response to the patient's atrioventricular interval exceeding the threshold interval; and
monitoring the patient's atrioventricular interval in response to the patient's atrioventricular interval not exceeding the threshold interval.

13. A method for heart failure management comprising:
monitoring one or more sensor-based parameters for a patient;
determining whether the one or more monitored sensor-based parameters indicate atrial tachycardia or atrial fibrillation;
delivering a first pacing therapy in response to the one or more sensor-based parameters indicating atrial tachycardia or atrial fibrillation;
determining whether the one or more monitored sensor-based parameters indicate the patient's P-wave duration exceeds a P-wave duration threshold value in response to the one or more sensor-based parameters not indicating atrial tachycardia or atrial fibrillation;
delivering a second pacing therapy in response to the one or more sensor-based parameters indicating the patient's P-wave duration exceeds a P-wave duration threshold value; and
delivering a third pacing therapy in response to the one or more sensor-based parameters not indicating the patient's P-wave duration exceeds a P-wave duration threshold value.

14. The method of claim 13, wherein the first pacing therapy comprises a first atrioventricular node stimulation sequence at a first voltage greater than a threshold value.

15. The method of claim 14, wherein the second pacing therapy comprises atrial pacing and a second atrioventricular node stimulation sequence at a second voltage less than the threshold value.

16. The method of claim 15, wherein the third pacing therapy comprises the second atrioventricular node stimulation sequence at a third voltage less than the threshold value.

17. A method for heart failure management comprising:
monitoring one or more sensor-based parameters for a patient;
determining whether the one or more monitored sensor-based parameters indicate the patient's P-wave duration exceeds a P-wave duration threshold value;
delivering a first atrioventricular node stimulation therapy in response to the one or more sensor-based parameters indicating the patient's P-wave duration exceeds a P-wave duration threshold value; and
delivering a second atrioventricular node stimulation therapy in response to the one or more sensor-based parameters not indicating the patient's P-wave duration exceeds a P-wave duration threshold value.

18. The method of claim 17, wherein the first atrioventricular node stimulation therapy comprises atrial pacing and an atrioventricular node stimulation sequence at a voltage less than a threshold.

19. The method of claim 18, wherein the second atrioventricular node stimulation therapy is the atrioventricular node stimulation sequence at a voltage less than the threshold.

20. The method of claim 17, further comprising:
determining whether the patient's atrioventricular interval exceeds a threshold interval in response to delivering the first or second atrioventricular node stimulation therapy;
delivering DDD mode pacing with a predetermined atrioventricular interval in response to the patient's atrioventricular interval exceeding the threshold interval; and
monitoring the patient's atrioventricular interval in response to the patient's atrioventricular interval not exceeding the threshold interval.

\* \* \* \* \*